(12) United States Patent
Zhu (10) Patent No.: US 10,043,087 B2
(45) Date of Patent: Aug. 7, 2018

(54) LIVING BODY IDENTIFICATION DEVICE, LIVING BODY IDENTIFICATION METHOD AND LIVING BODY AUTHENTICATION SYSTEM

(71) Applicant: BOE TECHNOLOGY GROUP CO., LTD., Beijing (CN)

(72) Inventor: Lin Zhu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 10 days.

(21) Appl. No.: 15/104,748

(22) PCT Filed: Jan. 5, 2016

(86) PCT No.: PCT/CN2016/070101
§ 371 (c)(1),
(2) Date: Jun. 15, 2016

(87) PCT Pub. No.: WO2017/000537
PCT Pub. Date: Jan. 5, 2017

(65) Prior Publication Data
US 2017/0193317 A1      Jul. 6, 2017

(30) Foreign Application Priority Data

Jul. 2, 2015    (CN) .......................... 2015 1 0382364

(51) Int. Cl.
*G06K 9/00*  (2006.01)
*A61B 5/04*  (2006.01)
(Continued)

(52) U.S. Cl.
CPC ........ *G06K 9/00906* (2013.01); *A61B 5/0044* (2013.01); *A61B 5/0059* (2013.01);
(Continued)

(58) Field of Classification Search
None
See application file for complete search history.

(56) References Cited

U.S. PATENT DOCUMENTS 7,596,247 B2 * 9/2009 Loffe ................. G06K 9/00281
340/5.53
8,270,680 B2 * 9/2012 Manabe ............. G06K 9/00033
382/115
(Continued)

FOREIGN PATENT DOCUMENTS

CN        101625616 A      1/2010
CN        101630213 A      1/2010
(Continued)

OTHER PUBLICATIONS

Holz, Christian, and Patrick Baudisch. "Fiberio: a touchscreen that senses fingerprints." Proceedings of the 26th annual ACM symposium on User interface software and technology. ACM, 2013.*
(Continued)

*Primary Examiner* — Andrae S Allison
(74) *Attorney, Agent, or Firm* — Nath, Goldberg & Meyer; Joshua B. Goldberg (57) ABSTRACT

The present invention provides a living body identification device, a living body identification method and a living body authentication system. The living body identification device comprises an acquisition unit and a processing unit; the acquisition unit is configured for emitting light towards a characteristic position of the living body and receiving light reflected from the characteristic position, then converting the light into an electrical signal, and sending the electrical signal to the processing unit; the acquisition unit comprises at least one light source and a plurality of photosensitive elements which are disposed at intervals; the processing unit is configured for generating an image of the characteristic position according to the electrical signal, and processing (Continued)

the image of the characteristic position to eventually obtain the characteristic information of the characteristic position, the characteristic information being used for uniquely identifying the living body.

18 Claims, 4 Drawing Sheets

(51) Int. Cl.
  *A61B 5/00* (2006.01)
  *A61B 5/117* (2016.01)
  *A61B 3/00* (2006.01)
  *A61B 5/024* (2006.01)
  *A61B 5/1172* (2016.01)
  *A61B 5/1171* (2016.01)

(52) U.S. Cl.
  CPC ............... *A61B 5/04* (2013.01); *A61B 5/117* (2013.01); *G06K 9/00* (2013.01); *G06K 9/00033* (2013.01); *G06K 9/00362* (2013.01); *A61B 3/00* (2013.01); *A61B 5/02416* (2013.01); *A61B 5/1172* (2013.01); *A61B 5/1176* (2013.01); *A61B 5/489* (2013.01); *A61B 2562/0233* (2013.01); *A61B 2562/046* (2013.01); *G06K 9/00006* (2013.01); *G06K 9/00013* (2013.01); *G06K 9/00885* (2013.01); *G06K 9/00892* (2013.01); *G06K 9/00899* (2013.01); *G06K 2009/00939* (2013.01)

(56) References Cited

U.S. PATENT DOCUMENTS

| | | | | |
|---|---|---|---|---|
| 8,369,595 B1 * | 2/2013 | Derakhshani | ........ | G06K 9/0061 382/117 |
| 8,483,450 B1 * | 7/2013 | Derakhshani | ...... | G06K 9/00597 382/115 |
| 8,718,362 B2 * | 5/2014 | Tuzel | ................ | G06K 9/4609 382/170 |
| 9,224,042 B2 * | 12/2015 | Venkatesha | ........ | G06K 9/00604 |
| 9,530,052 B1 * | 12/2016 | Pillai | .................. | G06K 9/00617 |
| 9,558,391 B2 | 1/2017 | Cheng et al. | | |
| 9,740,932 B2 * | 8/2017 | Venkatesha | ........ | G06K 9/00617 |
| 2003/0118217 A1 * | 6/2003 | Kondo | ............... | G06K 9/00604 382/117 |
| 2003/0228037 A1 | 12/2003 | Endo | | |
| 2010/0002008 A1 | 1/2010 | Tsuzaki et al. | | |
| 2014/0044321 A1 * | 2/2014 | Derakhshani | ...... | G06K 9/00597 382/117 |
| 2016/0019409 A1 * | 1/2016 | Cheng | ..................... | H04N 7/18 348/77 |

FOREIGN PATENT DOCUMENTS

| | | | |
|---|---|---|---|
| CN | 103329078 A | | 9/2013 |
| CN | 103559472 A | | 2/2014 |
| CN | 104091107 A | | 10/2014 |
| CN | 104951769 A | | 9/2015 |
| WO | WO2015005959 | * | 1/2015 |

OTHER PUBLICATIONS

International Search Report dated Mar. 24, 2016 corresponding to International application No. PCT/CN2016/070101.
Written Opinion of the International Searching Authority dated Mar. 24, 2016 corresponding to International application No. PCT/CN2016/070101.
Office Action dated Nov. 1, 2017 issued in corresponding to Chinese Application No. 201510382364.5.
Second Office Action dated Apr. 23, 2018 in corresponding Chinese Patent Application No. 201510382364.5.

* cited by examiner

LIVING BODY IDENTIFICATION DEVICE, LIVING BODY IDENTIFICATION METHOD AND LIVING BODY AUTHENTICATION SYSTEM

This is a National Phase Application filed under 35 U.S.C. 371 as a national stage of PCT/CN2016/070101, filed Jan. 5, 2016, an application claiming the benefit of Chinese Application No. 201510382364.5, filed on Jul. 2, 2015, the content of each of which is hereby incorporated by reference in its entirety.

FIELD OF THE INVENTION

The present invention relates to the field of living body identification technologies, and in particular to a living body identification device, a living body identification method and a living body authentication system.

BACKGROUND OF THE INVENTION

At present, methods for identifying a living body include: fingerprint identification, iris identification, face identification, vein recognition, heart rate identification and the like. Most of the fingerprint identification methods are based on the following principle: a fingerprint is acquired by a fingerprint acquisition unit, a fingerprint image is generated from the acquired fingerprint, then the fingerprint image is processed to extract fingerprint characteristic points, and finally the fingerprint characteristic points are stored for specific application of the fingerprint (for example, for use in fingerprint authentication).

Figure 1:
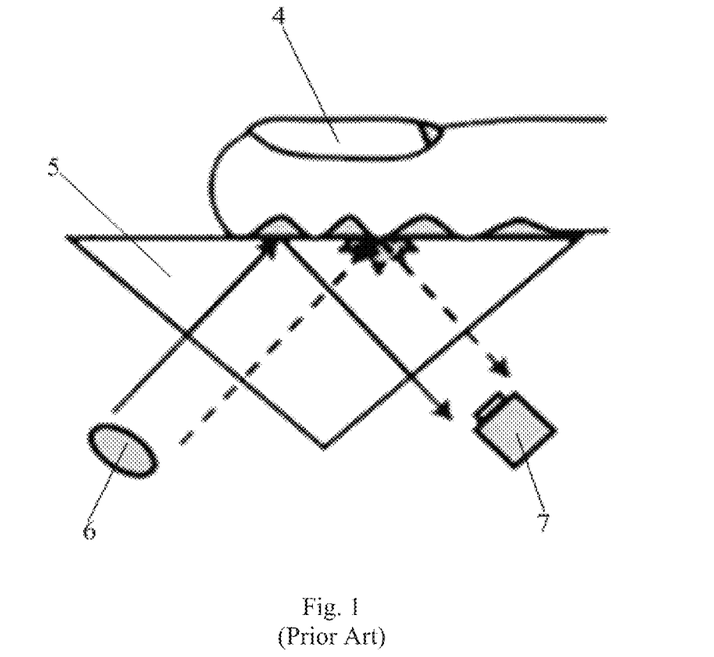
FIG. 1 is a schematic diagram of acquisition of a fingerprint by an optical fingerprint acquisition device in the prior art.

Traditional fingerprint acquisition methods include: optical fingerprint acquisition, capacitive fingerprint acquisition and ultrasonic fingerprint acquisition. FIG. 1 is a schematic structure diagram of a traditional optical fingerprint acquisition device, which mainly uses the refraction principle and the reflection principle of light. Specifically, a finger 4 is put on an optical lens 5 (for example, a triangular prism); when the finger 4 is exposed to light from a built-in light source 6, the light is incident into the optical lens from the bottom thereof and emergent from the optical lens; and the emergent light will have different refractive angle and brightness of reflected light on rugged lines of the fingerprint on the surface of the finger 4. The light is projected, by the optical lens, onto a sensor 7 (for example, a charge-coupled device) to form a digital multi-gray fingerprint image which can be processed by an algorithm of a fingerprint device and in which ridge lines (lines with certain width and trend in the fingerprint image) are presented as black and valley lines (recesses between ridges) are presented as white.

The light source 6 and the sensor 7 of this optical fingerprint acquisition device must be arranged at specific positions, and it is necessary to use the optical lens 5 so that light emitted from the light source 6 to the finger 4 can reach the sensor 7 after being reflected. Furthermore, only the light emitted in a specific angle from the light source 6 can be received by the sensor 7 after being reflected. That is, if light reflected from the optical lens deviates from the reception range of the sensor 7, fingerprint information cannot be acquired.

The aforementioned optical acquisition device requires direct contact between a part, which is to be identified, of a living body and the acquisition device, making the detection very inconvenient. In addition, usually, identification of an iris or a face cannot be achieved by this device, greatly limiting the application of such an optical acquisition device.

SUMMARY OF THE INVENTION

In view of the above-mentioned technical problems existing in the prior art, the present invention provides a living body identification device, a living body identification method and a living body authentication system. The living body identification device can identify a living body in both cases of contacting and not contacting a characteristic position of the living body, so that the characteristic position of the living body can realize applications such as authentication and touch control without contacting an acquisition unit. In this way, the living body identification device becomes more convenient and easier in identification and application.

The present invention provides a living body identification device for identifying characteristic information of a living body, including an acquisition unit and a processing unit; the acquisition unit is configured for emitting light towards a characteristic position of the living body and receiving light reflected from the characteristic position, then converting the received light into an electrical signal, and sending the electrical signal to the processing unit; the acquisition unit includes at least one light source and a plurality of photosensitive elements which are disposed at intervals; and the processing unit is configured for generating an image of the characteristic position according to the electrical signal, and processing the image of the characteristic position to eventually obtain the characteristic information of the characteristic position, the characteristic information being used for uniquely identifying the living body.

Preferably, the acquisition unit includes a transparent substrate and a plurality of light sources and a plurality of photosensitive elements arranged on a surface of the transparent substrate at one side, and the plurality of light sources are distributed at intervals, and the plurality of photosensitive elements are arranged in spaces between the light sources.

Preferably, the plurality of light sources are uniformly distributed, and the plurality of photosensitive elements are uniformly distributed.

Preferably, the plurality of light sources are arranged in a matrix, the plurality of photosensitive elements are each located in a space between any two light sources which are adjacent in row direction and/or column direction and/or diagonal direction, and the distances between each photosensitive element and the light sources adjacent to the photosensitive element are identical.

Preferably, a distance between two light sources which are adjacent in row or column direction ranges from 50 μm to 100 μm, the shape of the light sources includes rectangle, and the length of a side of the light sources ranges from 50 μm to 200 μm.

Preferably, a resolution of the photosensitive elements is more than 500 dpi, and a resolution of the light sources is more than 500 dpi.

Preferably, the distance between the acquisition unit and the characteristic position ranges from 1 mm to 10 cm.

Preferably, the light source includes a light-emitting diode, and the light-emitting diode includes a white light-emitting diode or a green light-emitting diode.

Preferably, the characteristic information includes vein information, heart rate information, fingerprint information, iris information or face information; and the vein information, the heart rate information and the fingerprint information can be acquired from a finger, and the iris information can be acquired from an eye, and the face information can be acquired from a face.

Preferably, an acquisition time duration of the heart rate information ranges from 20 seconds to 30 seconds, and acquisition time durations of the vein information, the fingerprint information, the iris information and the face information are less than 10 seconds.

Preferably, the processing unit includes an image generation module, an image processing module and a characteristic information extraction module;

the image generation module is configured for generating the image of the characteristic position according to the electrical signal, and sending the image of the characteristic position to the image processing module;

the image processing module is configured for performing fine calculation on the image of the characteristic position; and sending the processed image of the characteristic position to the characteristic information extraction module; and the characteristic information extraction module is configured for extracting the characteristic information from the processed image of the characteristic position.

Preferably, the living body identification device also includes a storage unit, which is connected to the processing unit and configured for storing the characteristic information which is eventually obtained after the processing of the processing unit.

The present invention also provides a living body authentication system, including the above-mentioned living body identification device.

Preferably, the living body authentication system also includes a characteristic information database and a matching module; the characteristic information database is configured for storing characteristic information of a plurality of living bodies; and the matching module is configured for matching the characteristic information obtained by the living body identification device with characteristic information in the characteristic information database, and authenticating the living body with successful match.

The present invention also provides a living body identification method using the above-mentioned living body identification device, including: emitting light towards a characteristic position of a living body; receiving light reflected from the characteristic position, and then converting the light into an electrical signal; and generating an image of the characteristic position according to the electrical signal, and processing the image of the characteristic position to eventually obtain characteristic information of the characteristic position, the characteristic information being able to uniquely identify the living body.

The present invention has the following beneficial effects: in the living body identification device provided by the present invention, by disposing a plurality of photosensitive elements at intervals, light with a larger angle, which is emitted to a characteristic position by the acquisition unit, can be received by the acquisition unit after being reflected by the characteristic position, so that information of the characteristic position can be acquired by the living body identification device in a more flexible way; meanwhile, since a plurality of photosensitive elements are disposed at intervals; an optical lens is no longer required to strictly control the direction of the reflected light, and instead, with a plurality of photosensitive elements which are disposed at intervals, the reflected light from the living body itself in the characteristic position can be received, so that the information of the characteristic position can be acquired by the living body identification device in both cases of contacting and not contacting the characteristic position. In this way, the characteristic position of the living body can realize applications such as authentication and touch control without contacting the acquisition unit; and thus the living body identification device becomes more convenient and easier in identification and application.

In the living body authentication system provided by the present invention, the above-mentioned living body identification device is adopted, so non-contact authentication can be achieved, and the living body authentication system can be used in a more convenient and easier way.

REFERENCE NUMERALS

1: acquisition unit; 11: transparent substrate; 12: light source; 13: photosensitive element; 2: processing unit; 21: image generation module; 22: image processing module; 23: characteristic information extraction module; 3: storage unit; 4: finger; 5: optical lens; 6: built-in light source; and 7: sensor.

DESCRIPTION OF THE PREFERRED EMBODIMENT

In order to make those skilled in the art better understand the technical solutions of the present invention, a living body identification device, a living body identification method and a living body authentication system provided by the present invention will be further described in detail below with reference to the accompanying drawings and specific embodiments.

Embodiment 1

Figure 2:
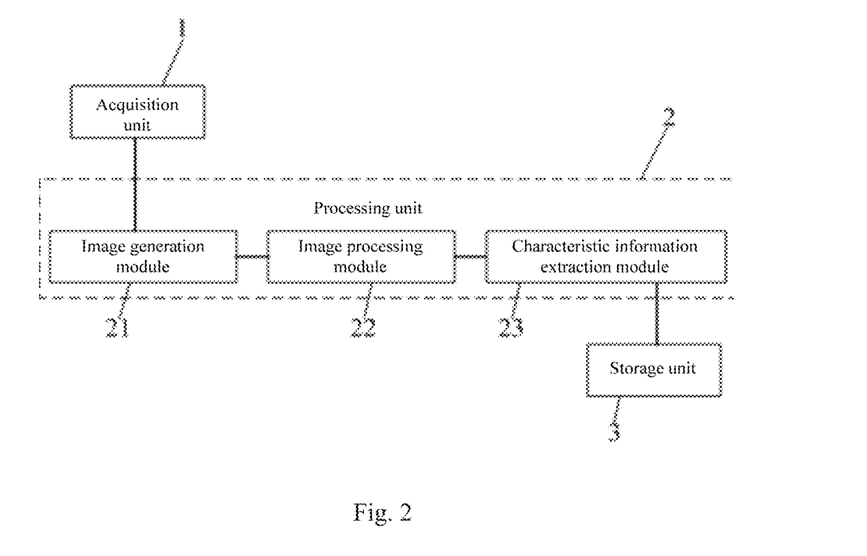
FIG. 2 is a schematic block diagram of a living body identification device according to Embodiment 1 of the present invention.

This embodiment provides a living body identification device for identifying characteristic information of a living body. As shown in FIG. 2, this device includes an acquisition unit 1 and a processing unit 2; the acquisition unit 1 is used for emitting light to a characteristic position of the living body and receiving light reflected from the characteristic position, then converting the light into an electrical signal, and sending the electrical signal to the processing unit 2; the acquisition unit 1 includes at least one light source and a plurality of photosensitive elements which are arranged at intervals; the processing unit 2 is used for generating an image of the characteristic position according to the electrical signal, and processing the image of the characteristic position to eventually obtain characteristic information of the characteristic position, the characteristic information being used for uniquely identifying the living body.

Figure 3:
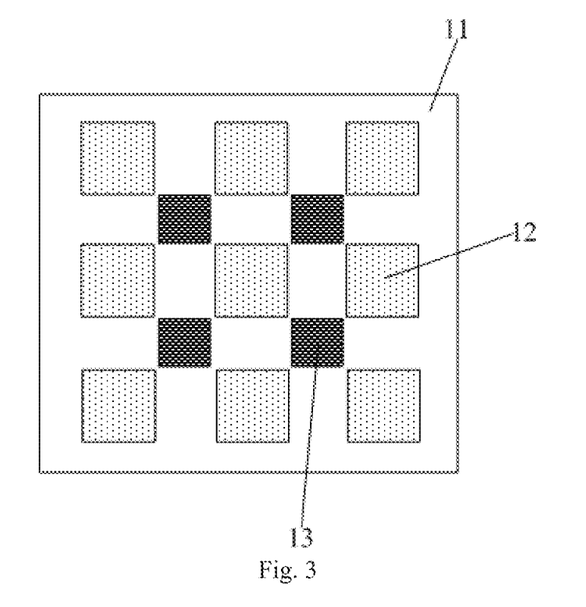
FIG. 3 is a schematic structure diagram of a first example of an acquisition unit in FIG. 2.
Figure 4:
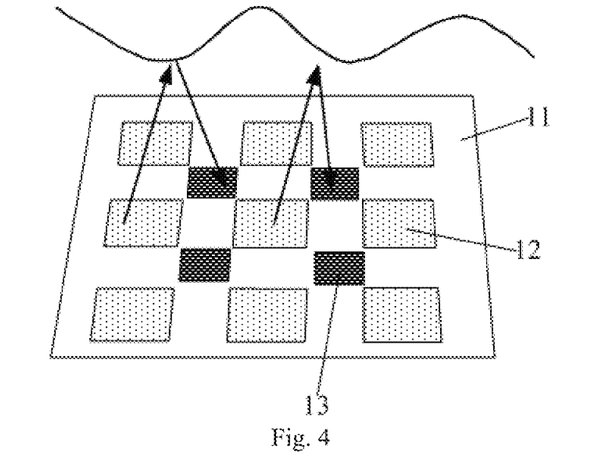
FIG. 4 is a schematic diagram of information acquisition of a characteristic position of a living body by the acquisition unit in FIG. 2.

A living body can be, for example, a human being or other living animal. Since the acquisition unit 1 includes a plurality of photosensitive elements which are arranged at intervals, light with a larger angle which is emitted to a characteristic position can be received by the acquisition unit 1 after being reflected. That is to say, an included angle between the light which is emitted to the characteristic position from the acquisition unit 1 and the light which is correspondingly reflected from the characteristic position can be larger, as compared with an included angle, which can only be a constant angle, between the emitted light and the reflected light in the prior art. In view of this, the living body identification device can acquire information of the characteristic position in a more flexible way; meanwhile; since a plurality of photosensitive elements are arranged at intervals, an optical lens is no longer required to strictly control the direction of the reflected light, and instead, with a plurality of photosensitive elements which are arranged at intervals, the reflected light of the living body at the characteristic point can be received, so that the information of the characteristic position can be acquired by the living body identification device in both cases of contacting and not contacting the characteristic position. In this way, the characteristic position of the living body can realize applications such as authentication and touch control without contacting the acquisition unit 1, and thus the living body identification device becomes more convenient and easier in living body identification and application In this embodiment, as shown in FIG. 3 and FIG. 4, the acquisition unit 1 includes a transparent substrate 11, and a plurality of light sources 12 and a plurality of photosensitive elements 13 arranged on a surface of one side of the transparent substrate 11; the light sources 12 are used for emitting light to the characteristic position; the photosensitive elements 13 are used for receiving light reflected from the characteristic position and converting the light into an electrical signal; and the plurality of light sources 12 are arranged at intervals, and the photosensitive elements 13 are also arranged at intervals and disposed in spaces between the light sources 12. Such an arrangement can make sure that light with a larger angle emitted by the light sources 12 to the characteristic position can be received by the photosensitive elements 13 after being reflected by the characteristic position.

The plurality of light sources 12 are uniformly distributed, and the plurality of photosensitive elements 13 are uniformly distributed. The uniform distribution of the plurality of light sources 12 can not only enables all the characteristic positions of the living body to be exposed to light, but can also make light irradiated onto these characteristic positions more uniform. The uniform distribution of the plurality of photosensitive elements 13 enables most of the light reflected by different positions among the characteristic positions to be sensed by the photosensitive elements 13. In addition, the light sources 12 and the photosensitive elements 13 are distributed on a same surface, and the photosensitive elements 13 are disposed in spaces between the light sources 12, so that light irradiated onto the characteristic position can be reflected exactly onto the photosensitive elements 13 after being reflected, so as to be sensed by the photosensitive elements 13. Based on this photosensitive principle, a distance between the characteristic position and the acquisition unit 1 can be adjusted at will, as long as light irradiated onto the characteristic position can be received and sensed by the photosensitive elements 13 after being reflected. Thus, even there is no contact between the characteristic position and the acquisition unit 1, light reflected from the characteristic position can also be received and sensed, thereby achieving the acquisition of characteristic position information.

It should be noted that, in this embodiment, the characteristic position can also contact the acquisition unit 1, and in this case, light reflected from the characteristic position can also be received and sensed, thereby achieving the acquisition of characteristic position information.

In this embodiment, the light sources 12 are arranged in a matrix, each of the photosensitive elements 13 is located in a space between any two diagonally-adjacent light sources 12, and the photosensitive element 13 is spaced from the two light sources 12 adjacent thereto at an equal distance. Such an arrangement can make sure that light with a larger angle, which is emitted to the characteristic position from the light sources 12 adjacent to the photosensitive elements 13, is incident into the photosensitive elements 13 after being reflected. In this way, it is ensured that information of the characteristic position can be acquired by the photosensitive elements 13.

Figure 5:
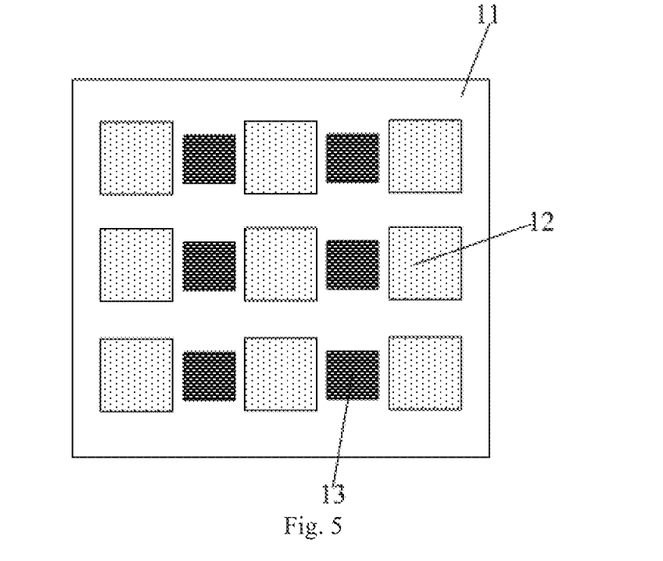
FIG. 5 is a schematic structure diagram of a second example of the acquisition unit in FIG. 2.
Figure 6:
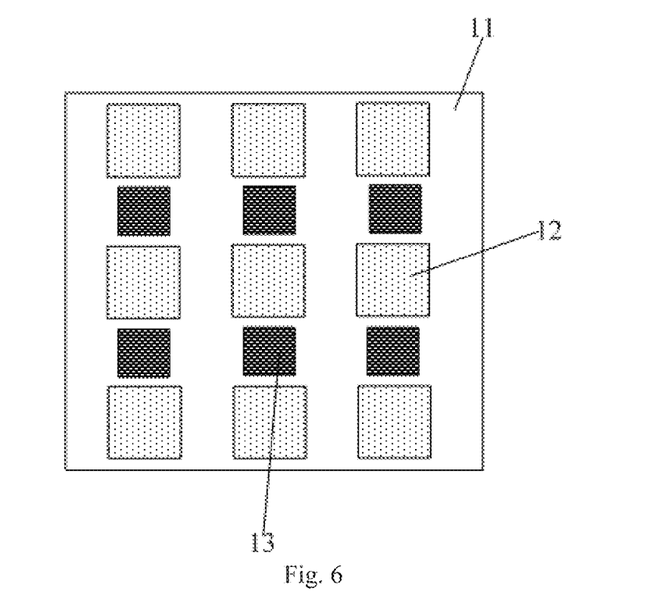
FIG. 6 is a schematic structure diagram of a third example of the acquisition unit in FIG. 2.

It should be noted that the photosensitive elements 13 each can also be located in a space between any two adjacent light sources 12 in a row direction (as shown in FIG. 5) or in a column direction (as shown in FIG. 6). In this way, it can also be ensured that light, which is emitted to the characteristic position from the light sources 12 adjacent to the photosensitive elements 13, is incident into the photosensitive elements 13 after being reflected, thus ensuring that information of the characteristic position can be acquired by the photosensitive elements 13.

Figure 7:
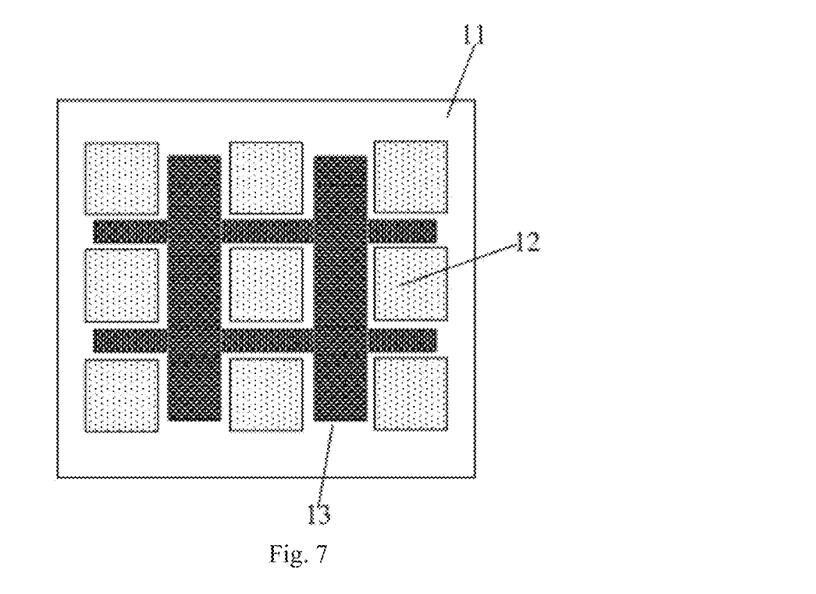
FIG. 7 is a schematic structure diagram of a fourth example of the acquisition unit in FIG. 2.

As shown in FIG. 7, a plurality of photosensitive elements 13 which are integrally connected can be arranged in the space between the light sources 12. Such an arrangement can make sure that light with a larger angle, which is emitted from the light sources 12, is received by the photosensitive elements 13 after being reflected. In this way, it is further ensured that information of the characteristic position can be acquired by the photosensitive elements 13.

In this embodiment, a distance between two light sources 12 which are adjacent in the row or column direction ranges from 50 μm to 100 μm, the shape of the light sources 12 includes rectangle, and the length of a side of the light sources 12 ranges from 50 μm to 200 μm. Of course, the shape of the light sources 12 can also be other shape, for example, circle or equilateral polygon. The shape of the photosensitive elements 13 is preferably rectangle, and can also be other shape, for example, circle or equilateral polygon.

In this embodiment, a resolution of the photosensitive elements 13 is more than 500 dpi, and a resolution of the light sources 12 is more than 500 dpi, wherein dpi (Dots Per Inch) refers to the number of light sources 12 or photosensitive elements 13 distributed per inch, and indicates the distribution density of light sources 12 or photosensitive elements 13. Such an arrangement can ensure a higher acquisition accuracy of information of the characteristic position so that the characteristic information of the characteristic position eventually obtained after the processing of a subsequent processing unit 2 is more accurate and clear.

In this embodiment, the distance between the acquisition unit 1 and the characteristic position ranges from 1 mm to 10 cm. Such a distance range enables the living body identification device to identify and apply the characteristic position more flexibly and conveniently. If the living body identification device can achieve three-dimensional control in the air (i.e., the characteristic position of the living body is moved in various directions in the air) in applications such as authentication or touch control of characteristic information of the characteristic position, the characteristic information of the characteristic position can be authenticated or touch devices such as a touch screen can be controlled by touch, correspondingly.

In this embodiment, a light source 12 includes a light-emitting diode (LED), and the light-emitting diode includes a white light-emitting diode or a green light-emitting diode. The white light-emitting diode and the green light-emitting diode are respectively applied to identify different characteristic information of a same characteristic position. Some characteristic information can be better identified by the white light-emitting diode, while some characteristic information can be better identified by the green light-emitting diode. That is, light-emitting diodes of different colors can be used in different applications, and since the sensibility of light of different colors varies in different applications, using light-emitting diodes of different colors in different applications can further enhance the accuracy of information acquisition in different applications. Meanwhile, the application of light-emitting diodes of different colors in different applications further expands the application range of the living body identification device.

In this embodiment, the characteristic information includes vein information, heart rate information, fingerprint information, iris information or face information. That is, the living body identification device can identify all the above-mentioned characteristic information of a living body, so as to identify a living body uniquely corresponding to certain characteristic information. A characteristic position includes a finger, an eye, or a face; and the vein information, the heart rate information and the fingerprint information can be acquired from the finger, the iris information can be acquired from the eye, and the face information can be acquired from the face.

The principle of acquiring information of the characteristic position is as follows: the characteristic information can be presented by a corresponding characteristic position in such a way that the surface of the characteristic position is in a rugged state. Light irradiated onto a characteristic position (for example, a finger, an eye, or a face) can be reflected by a rugged surface of the characteristic position to different extent, so the reflected light received by the photosensitive elements 13 has a different intensity. As such, the rugged surface of the characteristic position can be distinguished and processed to eventually obtain the characteristic information of the characteristic position. The characteristic information of the characteristic position of the living body uniquely corresponds to the living body. In view of this, by using the characteristic information of the characteristic position, the living body can be uniquely identified.

It should be noted that a white light-emitting diode is applicable to acquisition of vein information, fingerprint information, iris information and face information, since white light is more sensitive in acquiring the vein information, the fingerprint information, the iris information and the face information and thus can achieve a higher acquisition accuracy. A green light-emitting diode is applicable to acquisition of heart rate information, since green light is more sensitive in acquiring the heart rate information and thus can achieve a higher acquisition accuracy.

In this embodiment, an acquisition time duration of the heart rate information ranges from 20 seconds to 30 seconds, and acquisition time durations of the vein information, the fingerprint information, the iris information and the face information are less than 10 seconds. That is, different characteristic information can be acquired and identified by the living body identification device. However, during each identification process, only one type of characteristic information can be acquired and identified. According to different acquisition time durations of different characteristic information, different characteristic information of a living body can be acquired and identified successively, so that the living body can be uniquely identified and authenticated in a more accurate way by acquiring and identifying various types of characteristic information.

In this embodiment, as shown in FIG. 2, the processing unit 2 includes an image generation module 21, an image processing module 22 and a characteristic information extraction module 23; the image generation module 21 is used for generating an image of the characteristic position according to an electrical signal, and sending the image of the characteristic position to the image processing module 22; the image processing module 22 is used for performing fine calculation on the image of the characteristic position, and sending the processed image of the characteristic position to the characteristic information extraction module 23; and the characteristic information extraction module 23 is used for extracting the characteristic information from the processed image of the characteristic position. After the characteristic information of the characteristic position is extracted, the living body can be uniquely identified according to the characteristic information.

In this embodiment, the living body identification device also includes a storage unit 3 which is connected to the processing unit 2 and used for storing the characteristic information which is eventually obtained after the processing of the processing unit 2. The arrangement of the storage unit 3 facilitates the subsequent application of the living body identification device in authentication of the characteristic information of the living body or touch control of the characteristic information and the like. That is to say, in the subsequent application, the characteristic information of a characteristic position of a living body only needs to be compared with that in the storage unit 3, and applications such as authentication and touch control of the characteristic information can be achieved if the comparison result shows a successful match.

Figure 8:
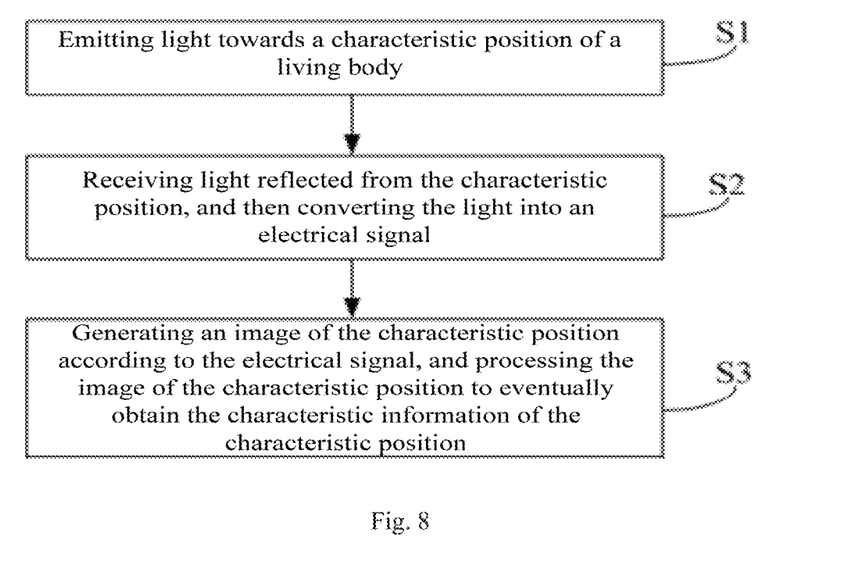
FIG. 8 is a flowchart of a living body identification method according to Embodiment 1 of the present invention.

Based on the above-described structure of the living body identification device of this embodiment, this embodiment also provides a living body identification method, as shown in FIG. 8, including:

step S1: emitting light to a characteristic position of a living body;

step S2: receiving light reflected from the characteristic position, and then converting the received light signal into an electrical signal; and step S3: generating an image of the characteristic position according to the electrical signal, and processing the image of the characteristic position to eventually obtain the characteristic information of the characteristic position, the characteristic information being able to uniquely identify the living body.

Embodiment 1 has the following beneficial effects: in the living body identification device provided in Embodiment 1, light with a larger angle, which is emitted to a characteristic position by the acquisition unit, can be all received by the acquisition unit after being reflected by the characteristic position, so that information of the characteristic position can be acquired by the living body identification device in a more flexible way; meanwhile, the living body identification device can acquire the information of the characteristic position in both cases of contacting and not contacting the characteristic position, so that applications such as authentication and touch control can be realized with the characteristic position of a living body not contacting an acquisition unit. In this way, the living body identification device becomes more convenient and easier in living body identification and application.

Embodiment 2

This embodiment provides a living body authentication system, including the living body identification device in Embodiment 1.

The living body authentication system also includes a characteristic information database and a matching module; the characteristic information database is used for storing characteristic information of a plurality of living bodies; and the matching module is used for matching the characteristic information obtained by the living body identification device with characteristic information in the characteristic information database, and authenticating the living body with successful match.

With the living body identification device in Embodiment 1, non-contact authentication can be achieved by the living body authentication system, so that the living body authentication system can be used in a more convenient and easier way.

It should be understood that the above-mentioned embodiments are merely exemplary embodiments provided for describing the principle of the present invention, and the present invention is not limited thereto. For a person of ordinary skill in the art, various variations and improvements can be made without departing from the spirit and scope of the present invention, and these variations and improvements shall be regarded as Balling into the protection scope of the present invention.

The invention claimed is:

1. A living body identification device for identifying characteristic information of a living body, comprising an acquisition unit and a processing unit, wherein, the acquisition unit is configured for emitting light towards a characteristic position of the living body and receiving light reflected from the characteristic position, then converting the received light into an electrical signal, and sending the electrical signal to the processing unit; and the acquisition unit comprises at least one light source and a plurality of photosensitive elements which are disposed at intervals; and the processing unit is configured for generating an image of the characteristic position according to the electrical signal, and processing the image of the characteristic position to eventually obtain the characteristic information of the characteristic position, the characteristic information being used for uniquely identifying the living body, wherein the acquisition unit comprises a transparent substrate and a plurality of light sources and a plurality of photosensitive elements arranged on a surface of the transparent substrate at one side, the light sources being configured for emitting light towards the characteristic position, the photosensitive elements being configured for receiving the light reflected from the characteristic position and converting the received light into an electrical signal; and the plurality of light sources are distributed at intervals, and the plurality of photosensitive elements are arranged in spaces between the light sources, which can make sure that light with a larger angle emitted by the plurality of light sources to the characteristic position can be received by the plurality of photosensitive elements after being reflected by the characteristic position.

2. The living body identification device according to claim 1, wherein the plurality of light sources are uniformly distributed, and the plurality of photosensitive elements are uniformly distributed.

3. The living body identification device according to claim 2, wherein the plurality of light sources are arranged in a matrix, the plurality of photosensitive elements are each located in a space between any two light sources which are adjacent in row direction and/or column direction and/or diagonal direction, and the distances between the photosensitive elements and the light sources adjacent to the photosensitive elements are identical.

4. The living body identification device according to claim 3, wherein the distance between two light sources which are adjacent in row or column direction ranges from 50 μm to 100 μm, the shape of the light sources comprises rectangle, and the length of a side of the light sources ranges from 50 μm to 200 μm.

5. A living body authentication system, comprising the living body identification device of claim 4.

6. A living body authentication system, comprising the living body identification device of claim 3.

7. The living body identification device according to claim 2, wherein a resolution of the photosensitive elements is more than 500 dpi, and a resolution of the light sources is more than 500 dpi.

8. A living body authentication system, comprising the living body identification device of claim 7.

9. The living body identification device according to claim 2, wherein the light source comprises a light-emitting diode, and the light-emitting diode comprises a white light-emitting diode or a green light-emitting diode.

10. A living body authentication system, comprising the living body identification device of claim 2.

11. The living body identification device according to claim 1, wherein the distance between the acquisition unit and the characteristic position ranges from 1 mm to 10 cm.

12. The living body identification device according to claim 1, wherein the characteristic information comprises vein information, heart rate information, fingerprint information, iris information or face information; and the vein information, the heart rate information and the fingerprint information are acquired from a finger, the iris information is acquired from an eye, and the face information is acquired from a face.

13. The living body identification device according to claim 12, wherein an acquisition time duration of the heart rate information ranges from 20 seconds to 30 seconds, and acquisition time durations of the vein information, the fingerprint information, the iris information and the face information are less than 10 seconds.

14. The living body identification device according to claim 1, wherein the processing unit comprises an image generation module, an image processing module and a characteristic information extraction module;

the image generation module is configured for generating the image of the characteristic position according to the electrical signal, and sending the image of the characteristic position to the image processing module;

the image processing module is configured for performing fine calculation on the image of the characteristic position, and sending the processed image of the characteristic position to the characteristic information extraction module; and the characteristic information extraction module is configured for extracting the characteristic information from the processed image of the characteristic position.

15. The living body identification device according to claim 1, further comprising a storage unit, which is connected to the processing unit and configured for storing the characteristic information which is eventually obtained after the processing of the processing unit.

16. A living body authentication system, comprising the living body identification device of claim 1.

17. The living body authentication system according to claim 16, further comprising a characteristic information database and a matching module; the characteristic information database is configured for storing characteristic information of a plurality of living bodies; and the matching module is configured for matching the characteristic information obtained by the living body identification device with characteristic information in the characteristic information database, and authenticating the living body with successful match.

18. A living body identification method using the living body identification device according to claim 1, comprising:

emitting light towards a characteristic position of a living body;

receiving light reflected from the characteristic position, and then converting the light into an electrical signal; and generating an image of the characteristic position according to the electrical signal, and processing the image of the characteristic position to eventually obtain characteristic information of the characteristic position, the characteristic information being able to uniquely identify the living body.

* * * * *